United States Patent [19]
Deege et al.

[11] Patent Number: 5,912,206
[45] Date of Patent: Jun. 15, 1999

[54] HERBICIDAL COMPOSITIONS

[75] Inventors: Rolf Deege, Leverkusen, Germany; Jean-Claude Millet, Ecully, France

[73] Assignee: Rhone-Poulenc Agrochimie, Lyon Cedex, France

[21] Appl. No.: 08/849,339

[22] PCT Filed: Dec. 1, 1995

[86] PCT No.: PCT/EP95/04752

§ 371 Date: Aug. 22, 1997

§ 102(e) Date: Aug. 22, 1997

[87] PCT Pub. No.: WO96/17519

PCT Pub. Date: Jun. 13, 1996

[30] Foreign Application Priority Data

Dec. 9, 1994 [GB] United Kingdom .............. 94 28453

[51] Int. Cl.⁶ .............................. A01N 43/36; A01N 43/72
[52] U.S. Cl. ..................................... 504/138; 504/139
[58] Field of Search ..................... 504/138, 139

[56] References Cited

U.S. PATENT DOCUMENTS

| | | | |
|---|---|---|---|
| 4,968,342 | 11/1990 | Förster et al. | 71/90 |
| 5,090,991 | 2/1992 | Förster et al. | 71/90 |
| 5,593,942 | 1/1997 | Santel et al. | 504/134 |

FOREIGN PATENT DOCUMENTS

| | | |
|---|---|---|
| 0348737 | 1/1990 | European Pat. Off. . |
| 0418175 | 3/1991 | European Pat. Off. . |
| 0487357 | 5/1992 | European Pat. Off. . |
| 0527036 | 2/1993 | European Pat. Off. . |
| 0560482 | 9/1993 | European Pat. Off. . |
| 4223465 | 1/1994 | Germany . |

OTHER PUBLICATIONS

Limpel et al, 1. *Proc. NEWCC 16*, pp. 48–53 (1962).
Colby, *Weeds 15*, pp. 20–22 (1967).

*Primary Examiner*—Allen J. Robinson
*Attorney, Agent, or Firm*—Burns, Doane, Swecker & Mathis, L.L.P.

[57] ABSTRACT

The invention relates to compositions comprising:
a) a 4-benzoylisoxazole of formula (I) wherein R, $R^1$ and $R^2$ are as defined in the description; and
b) N-isopropyl-(5-trifluoromethyl-1,3,4-thiadiazol-2-yl)-4-(4'-fluoro-oxyacetanilide) having formula (II)
and to their use as herbicides.

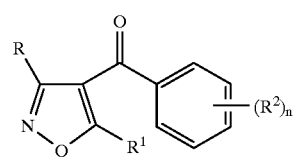

(I)

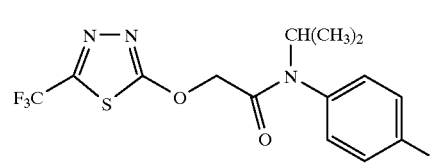

(II)

16 Claims, No Drawings

HERBICIDAL COMPOSITIONS

This application is a 371 of PCT/EP95/04752, filed Dec. 01, 1995.

TECHNICAL FIELD

This invention relates to new compositions comprising an N-isopropylheteroaryloxyacetanilide herbicide and a 4-benzoylisoxazole derivative, and to their use as herbicides.

BACKGROUND ART

The compounds of the invention are known in the art. N-Isopropylheteroaryloxyacetanilides are described in European Patent Publication Number 0348737, published on Jan. 3, 1990, which in particular discloses N-isopropyl-(5-trifluoromethyl-1,3,4-thiadiazol-2-yl)-(4'-fluoro-oxyacetanitide) as compound 34. 4-Benzoylisoxazoles are described in for example European Patent Publication Numbers 0418175, 0487357, 0527036 and 0560482. In particular, European Patent Publication Number 0560482, published on Feb. 10, 1993, discloses 5-cyclopropyl-4-(2-methylsulphonyl-4-trifluoromethylbenzoyl)isoxazole. Each of these publications teach that these compounds possess herbicidal activity. However, neither of the publications teach specific anti-gramineous properties in the compounds. EP-A1-0348737 teaches that the acetanilide compounds may be applied at from 0.01 to 10 kg of active compound per hectare of soil surface, preferably 0.05 to 5 kg per ha; no details of the precise dose rates used for the application of the compounds to treat graminea EP-A1-0527036 teaches that the compounds of the invention possess high activity in comparison with known compounds against certain weed species.

Hence the literature does not teach mixtures of these compounds; nor does it suggest that such a mixture would be expected to be particularly usefull as an anti-graminicide. At present the most commonly used mixture in this area of weed science comprises metolachlor and atrazine. These are frequently recommended for use at dose rates from about 1 to 2.5 kg/ha of metolachlor and from 0.5 to 2.5 kg/ha of atrazine. An object of the invention is thus to provide a mixture suitable as a graminicide which may be used at reduced dose rates of active compound in comparison with the known products.

Remarkably, it has been found that the mixture of N-isopropyl-(5-trifluoromethyl-1,3,4-thiadiazol-2-yl)-4-(4'-fluoro-oxyacetanihide) with 4-benzoylisoxazole derivatives provides effective control of an extremely wide range of both monocotyledon and dicotyledon weeds at reduced dose rates when compared with these known compounds. Moreover it provides effective control together with selectivity in important crop species such as maize.

Surprisingly, and in addition to this, it has been found that in certain conditions the combined herbicidal activity of certain 4-benzoylisoxazoles with N-isopropyl-(5-trifluoromethyl-1,3,4-thiadiazol-2-yl)-4-(4'-fluoro-oxyacetaanilde) for the control of certain weed species e.g. *Setaria viridis, Echinochloa crus-galli, Amaranthius retroflexus* and *Polygonum lapathifolium*, is greater than expected, without an unacceptable increase in crop phytotoxicity, i.e the mixture shows synergism as defined by Limpel, L. E., P. H. Schuldt and D. Lamont, 1962, 1. Proc. NEWCC 16, 48–53, also known as the Colby formula (Colby S. R., 1967, Weeds 15, 20–22), using the formula:

$$E = X + Y - \frac{XY}{100}$$

where
- E=the expected percent inhibition of growth by a mixture of two herbicides A and B at defined doses.
- X=the percent inhibition of growth by herbicide A at a defined dose.
- Y=the percent inhibition of growth by herbicide B at a defined dose.

When the observed percentage of inhibition by the mixture is greater than the expected value E using the formula above the combination is synergistic.

This remarkable synergistic effect gives improved reliability in controlling these competitive weeds of many crop species, and contributes to a considerable reduction in the amount of active ingredient required for weed control.

DISCLOSURE OF INVENTION

According to the present invention there is provided a method of controlling the growth of weeds at a locus which comprises applying to said locus a herbicidally effective amount of:

(a) a 4-benzoylisoxazole of formula (I):

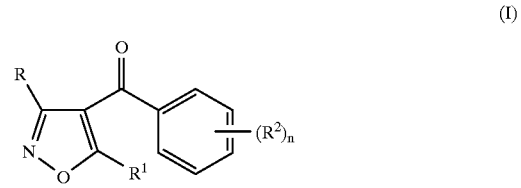

(I)

wherein
R is hydrogen or —$CO_2R^3$;
$R^1$ is cyclopropyl;
$R^2$ is selected from halogen, —$S(O)_p$Me and trifluoromethyl,
n is two or three; p is zero, one or two; and
$R^3$ is $C_{1-4}$ alkyl; and (b) N-isopropyl-(5-trifluoromethyl-1,3,4-thiadiazol-2-yl)-4-(4'-fluoro-oxyacetanilide) having the formula (II):

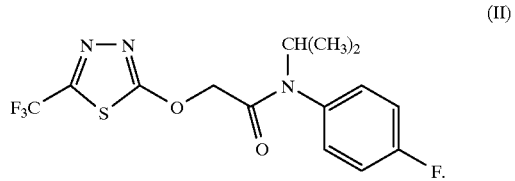

(II)

Preferably the 4-benzoylisoxazole derivative of formula (I) is 5-cyclopropyl-4-(2-methylsulphonyl-4-trifluoromethyl)-benzoylisozaxole, hereafter referred to as Compound A. For convenience N-isopropyl-(5-trifluoromethyl-1,3,4-thiadiazol-2-yl)-4-(4'-fluoro-oxyacetanilide) is hereafter referred to as compound B.

The amounts of the 4-benzoylisoxazole and compound B applied vary depending on the weeds present and their population, the compositions used, the timing of the application, the climatic and edaphic conditions, and (when used to control the growth of weeds in crop growing areas)

the crop to be treated. In general, taking these factors into account, application rates from 5 to 500 g of 4-benzoylisoxazole and from 10 to 10,000 g of compound B per hectare give good results. However, it will be understood that higher or lower application rates may be used, depending upon the problem of weed control encountered.

The method of the invention is most preferably used for the control of weeds at a locus used, or to be used for the growing of a crop. When applied to a crop-growing area, the rate of application should be sufficient to control the growth of weeds without causing substantial permanent damage to the crop.

Crops which the mixture may be used with include soyabeans, sugarcane, cotton, maize, sunflower, peas, chickpeas, potatoes, sorghum rice and cereals. The preferred crop, in terms of the selectivity of the mixture, is maize. For the selective control of weeds at a locus of weed infestation which is an area used, or to be used, for growing of crops application, rates from about 5 to 200 g of 4-benzoylisoxazole and from about 50 to 5,000 g of compound B per hectare are particularly suitable, preferably from about 50 to 130 g of 4-benzoylisoxazole and from about 80 to 875 g of compound B per hectare, most preferably from 75 to 100 g (about 80 g being most preferred) of 4-benzoylisoxazole and from 300 to 500 g (about 360 g being most preferred under humid conditions and about 450 g under more dry conditions) of compound B per hectare.

The mixture is preferably applied pre-emergence but can also be applied post-emergence (especially at an early stage of weed growth). By the term 'pre-emergence application' is meant application to the soil in which the weed seeds or seedlings are present before emergence of the crop. One example of a pre-emergence application is known as 'pre-plant incorporated' (PPI), where the herbicide is incorporated into the soil before planting the crop. Early PPI application may also be used. The mixture may also be applied pre-planting (i.e. before the crop is planted) either to the surface of the soil or soil-incorporated. Early pre-plant treatments using the mixture (particularly surface applied) are also a feature of the method of the invention.

According to a further feature of the present invention there are provided herbicidal compositions comprising:
(a) a 4-benzoylisoxazole derivative of formula I as defined above; and
(b) N-isopropyl-(5-trifluoromethyl-1,3,4-thiadiazol-2-yl)-4-(4'-fluoro-oxyacetanilide);
in association with, and preferably homogeneously dispersed in, a herbicidally acceptable diluent or carrier and/or surface active agent.

The term "herbicidal composition" is used in a broad sense, to include not only compositions which are ready for use as herbicides but also concentrates which must be diluted before use. Preferably, the compositions contain from 0.05 to 90% by weight of 4-benzoylisoxazole and compound B.

Unless otherwise stated, the percentages and ratios appearing in this specification are by weight.

Generally a composition in which the ratio of (a):(b) is from about 1:2000 to 50:1 wt/wt is used, proportions from about 1:1000 to 4:1 wt/wt being preferred, with proportions from about 1:17.5 to 1.63:1 wt/wt being more preferred, and proportions from about 1:6.67 to 1:3 wt/wt being especially preferred (ratios of about 1:4.5 in humid conditions and about 1:5.6 in dry conditions being most preferred).

The preferred formulation according to the invention is in the form of a water dispersible granule, although it will be understood that other formulation types known in the art may also be used.

In accordance with the usual practice, a tank mix may be prepared prior to use by combining separate formulations of the individual herbicidal components.

According to a further feature of the present invention, there is provided a product comprising:
(a) 4-benzoylisozaxole of formula I as defined above; and
(b) N-isopropyl-(5-trifluoromethyl-1,3,4-thiadiazol-2-yl)-4-(4'-fluoro-oxyacetanilide),
as a combined preparation for simultaneous, separate or sequential use in controlling the growth of weeds at a locus.

The following non-limiting experiments illustrate the present invention.

Experiment A1

The following experiments were conducted on Compound A and Compound B in various field research stations in Europe during May. Compound A (as a 750 g/kg water dispersible granule formulation) and Compound B (as a 600 g/kg water dispersible granule formulation) were tested at the following dose rates (note that hereafter ai means active ingredient):

| | |
|---|---|
| Compound A: | 50, 75, 100, 125 g ai/ha |
| Compound B: | 240, 366, 480, 600 g ai/ha |
| Compound A + Compound B: | 50 + 240/360/480 g ai/ha |
| | 75 + 240/360/480 g ai/ha |
| | 100 + 240/360/480 g ai/ha |

Trial and application conditions are given below in Table 1 (in the Tables that follow DAT means days after treatment):

TABLE 1

| LOCATION → | Chazay D'azergues France | Alzonne France | Bologna Italy |
|---|---|---|---|
| Soil texture | | | sandy loam |
| % Org. matter | 1.8 | 1.4 | 1.82 |
| pH | 6.9 | 7.9 | 8.13 |
| % Sand | 38 | 34 | 34 |
| % Silt | 41 | 39 | 46 |
| % Clay | 17 | 22 | 29 |
| Rainfall mm 15/30 DAT | 25/19 | 37/55 | 24/146 |
| Temperature (when applied) | 13° C. | 18° C. | 19° C. |
| Soil | WET | DRY | DRY |

Weeds were drilled on the same day as maize. All trials were sprayed pre-emergence of the maize on the same day as drilling or within 2 days afterwards. Soil conditions were warm and wet, so that the crop and weeds emerged and grew quickly. Rainfall or irrigation occurred within 15 days of application. The results are expressed as a percentage phytotoxicity, as shown in Table 2 below. In this Table "Obs" is the observed value the value in brackets (Exp) is the expected value calculated using the Colby formula.

Results:

TABLE 2

| Species<br>Dose rate<br>(g a.i./ha) | Echinochloa<br>crus-galli<br>ALZONNE<br>Obs (Exp)<br>46DAT | Echinochloa<br>crus-galli<br>BOLOGNA<br>Obs (Exp)<br>54DAT | Setaria<br>viridis<br>BOLOGNA<br>Obs (Exp)<br>54DAT | Amaranthus<br>retroflexus<br>ALZONNE<br>Obs (Exp)<br>46DAT | Polygonum<br>lapathifolium<br>CHAZAY<br>Obs (Exp)<br>64DAT |
|---|---|---|---|---|---|
| Cpd A | | | | | |
| 50 | 45 | 77 | 62 | 72 | 50 |
| 75 | 35 | 91 | 82 | 70 | 90 |
| 100 | 82 | 75 | 82 | 80 | 70 |
| 125 | 85 | 100 | 97 | 95 | 95 |
| Cpd B | | | | | |
| 240 | 45 | 35 | 85 | 30 | 25 |
| 360 | 65 | 52 | 82 | 10 | 0 |
| 480 | 77 | 65 | 86 | 67 | 25 |
| 600 | 90 | 75 | 82 | 45 | 40 |
| Cpd A + B | | | | | |
| 50 + 240 | 75 (70) | 100 (85) | 100 (94) | 95 (80) | 100 (62) |
| 75 + 240 | 90 (64) | 100 (99) | 100 (97) | 95 (79) | 90 (92) |
| 100 + 240 | 92 (90) | 100 (84) | 100 (97) | 84 (86) | 90 (77) |
| 50 + 360 | 87 (81) | 100 (89) | 100 (93) | 100 (75) | 95 (50) |
| 75 + 360 | 100 (77) | 100 (96) | 100 (97) | 92 (73) | 100 (90) |
| 100 + 360 | 100 (94) | 100 (88) | 100 (97) | 90 (82) | 100 (70) |
| 50 + 480 | 95 (87) | 100 (92) | 100 (95) | 87 (91) | 65 (62) |
| 75 + 480 | 85 (85) | 100 (97) | 100 (97) | 92 (90) | 100 (92) |
| 100 + 480 | 100 (96) | 100 (91) | 100 (97) | 85 (93) | 100 (77) |

The Colby formula may be applied to the above data and indicates that in 29 cases a better than expected level of weed control was observed (i.e. a synergistic interaction), in 2 cases a lower level of activity than expected was observed (i.e. antagonism) and in 14 cases the observed value was within 3% of the expected value (i.e. an additive effect). This clearly shows that in these trials the vast majority of the results were synergistic.

Experiment A2

The following experiments were conducted on the Compound A and Compound B in various field research stations in the United States. Compound A (as a 750 g/kg water dispersible granule formulation) and Compound B (as a 600 g/kg water dispersible granule formulation) were tested at the following dose rates:

| Compound B + Compound A: | 240 + 75/100/125 g ai/ha |
|---|---|
| | 360 + 75/100/125 g ai/ha |
| | 480 + 75/100/125 g ai/ha |

-continued

| Compound A: | 75/100/125/150 g ai/ha |
|---|---|
| Compound B: | 240/360/480/600 g ai/ha |

A commercial standard was also applied comprising metolachlor and atrazine at 1120/1120 g ai/ha and 2240/2240 g ai/ha of metolachlor/atrazine. The trials were conducted in South Dakota (1 trial), Nebraska (1), Iowa (1), Indiana (1), Pennsylvania (1) and Mississippi (1). The weed species were seeds in all locations. All trials were sprayed in May/June on the same day or within 3 days of maize sowing. In all trials, significant rainfalls or irrigation occurred shortly after spraying and for the next 2 or 3 weeks. The field trial and application conditions were as shown in Table 3 below:

TABLE 3

| LOCATION | S Dakota | Nebraska | Iowa | Pennsylvania | Mississippi | Indiana |
|---|---|---|---|---|---|---|
| Soil texture | silt loam | silt loam | silt loam | loam | clay | silt loam |
| % Org. Matter | 4.1 | 3.3 | 4 | 3 | 2.4 | 1.9 |
| pH | 6.1 | 6.4 | 7 | 6.9 | 6 | 6.2 |
| % Sand | 24 | 18 | 18 | 34 | 5.5 | — |
| % Silt | 52 | 58 | 56 | 44 | 38 | — |
| % Clay | 24 | 24 | 26 | 22 | 56 | — |
| Rainfall mm 15/30DAT | 81/108 | 19/49 | 51/83 | 62/28 | 78/15 | 27/146 |
| Soil temp. (appln) | 18° C. | 26° C. | 25° C. | 20° C. | 24° C. | |
| SOIL (appln) | MOIST | MOIST | | DRY | DRY | |

The mean results of the trials as a percentage of reduction in the growth of plant species at various stages after treatment are presented in Tables 4 to 6 below. Note that in the Tables the weed species are represented by the following Bayer codes and that ATR means Atrazine and MET means metolachlor.

| | |
|---|---|
| ABUTH = | Abutilon theophrasti |
| AMARE = | Amaranthus retroflexus |
| CHEAL = | Chenopodium album |
| DATST = | Datura stramonium |
| DIGSA = | Digitaria sanguinalis |
| ECHCG = | Echinochloa crus-galli |
| HELAN = | Helianthus annuus |
| IPOLA = | Ipomoea lacunosa |
| PANMI = | Panicum miliaceum |
| POLCO = | Polygonum convolvulus |
| SETFA = | Setaria faberi |
| SETLU = | Pennisetum glaucum |
| SETVI = | Setaria viridis |
| SORVU = | Sorghum vulgare |
| XANST = | Xanthium strumarium |

TABLE 4

| Dose Rates (g a.i/ha) | | 15DAT | 25DAT | 43DAT | 25DAT | 43DAT | 25DAT | 43DAT | 25DAT | 43DAT | 25DAT | 43DAT |
|---|---|---|---|---|---|---|---|---|---|---|---|---|
| Cpd A | Cpd B | Maize | Maize | Maize | ABUTH | ABUTH | AMARE | AMARE | CHEAL | CHEAL | DATST | DATST |
| 75 | 0 | 0 | 0 | 0 | 97 | 98 | 97 | 96 | 99 | 100 | 88 | 93 |
| 97.5 | 0 | 0 | 0 | 0 | 98 | 98 | 100 | 99 | 100 | 100 | 88 | 90 |
| 127.5 | 0 | 0 | 0 | 1 | 99 | 99 | 99 | 99 | 100 | 100 | 90 | 93 |
| 150 | 0 | 1 | 1 | 2 | 99 | 97 | 100 | 100 | 100 | 100 | 93 | 95 |
| 0 | 240 | 0 | 0 | 0 | 12 | 10 | 49 | 52 | 56 | 47 | 40 | 63 |
| 0 | 360 | 0 | 0 | 0 | 16 | 13 | 49 | 52 | 64 | 56 | 42 | 55 |
| 0 | 480 | 0 | 0 | 0 | 18 | 22 | 66 | 54 | 68 | 49 | 67 | 70 |
| 0 | 600 | 0 | 2 | 0 | 26 | 18 | 66 | 61 | 69 | 55 | 63 | 60 |
| 75 | 240 | 0 | 0 | 0 | 96 | 96 | 98 | 98 | 100 | 100 | 85 | 88 |
| 75 | 360 | 0 | 0 | 0 | 98 | 97 | 100 | 99 | 100 | 100 | 88 | 88 |
| 75 | 480 | 0 | 0 | 0 | 97 | 98 | 99 | 99 | 99 | 100 | 97 | 97 |
| 97.5 | 240 | 0 | 1 | 1 | 99 | 98 | 100 | 99 | 100 | 100 | 92 | 95 |
| 97.5 | 360 | 0 | 1 | 0 | 98 | 97 | 98 | 98 | 100 | 100 | 92 | 97 |
| 97.5 | 480 | 0 | 1 | 1 | 99 | 98 | 99 | 100 | 100 | 100 | 93 | 90 |
| 127.5 | 240 | 1 | 1 | 1 | 99 | 99 | 99 | 98 | 100 | 100 | 93 | 95 |
| 127.5 | 360 | 1 | 1 | 3 | 100 | 100 | 100 | 100 | 100 | 100 | 93 | 95 |
| 127.5 | 480 | 0 | 1 | 0 | 99 | 99 | 99 | 99 | 100 | 100 | 95 | 97 |
| ATR + MET – 1120 + 1120 | | 0 | 0 | 0 | 63 | 50 | 99 | 99 | 98 | 100 | 92 | 97 |
| ATR + MET – 2240 + 2240 | | 0 | 0 | 0 | 85 | 68 | 100 | 99 | 100 | 100 | 97 | 98 |

TABLE 5

| Dose Rates (g a.i/ha) | | 25DAT | 25DAT | 43DAT | 25DAT | 43DAT | 25DAT | 43DAT | 25DAT | 43DAT | 25DAT | 43DAT |
|---|---|---|---|---|---|---|---|---|---|---|---|---|
| Cpd A | Cpd B | DIGSA | ECHCG | ECHCG | HELAN | HELAN | IPOLA | IPOLA | PANMI | PANMI | POLCO | POLCO |
| 75 | 0 | 97 | 96 | 91 | 40 | 45 | 58 | 55 | 75 | 68 | 7 | 0 |
| 97.5 | 0 | 99 | 98 | 98 | 75 | 74 | 55 | 48 | 87 | 83 | 7 | 0 |
| 127.5 | 0 | 99 | 99 | 98 | 91 | 84 | 72 | 65 | 88 | 88 | 0 | 0 |
| 150 | 0 | 99 | 99 | 99 | 88 | 97 | 65 | 65 | 91 | 94 | 10 | 0 |
| 0 | 240 | 90 | 91 | 88 | 0 | 0 | 27 | 37 | 18 | 18 | 0 | 0 |
| 0 | 360 | 94 | 98 | 97 | 0 | 0 | 25 | 40 | 35 | 24 | 0 | 0 |
| 0 | 480 | 99 | 99 | 99 | 0 | 0 | 48 | 48 | 38 | 30 | 0 | 0 |
| 0 | 600 | 98 | 99 | 91 | 5 | 3 | 47 | 43 | 47 | 36 | 7 | 0 |
| 75 | 240 | 99 | 99 | 98 | 55 | 43 | 67 | 53 | 71 | 65 | 3 | 0 |
| 75 | 360 | 99 | 99 | 98 | 60 | 52 | 57 | 50 | 84 | 74 | 10 | 7 |
| 75 | 480 | 100 | 100 | 100 | 72 | 75 | 75 | 55 | 83 | 81 | 5 | 0 |
| 97.5 | 240 | 99 | 99 | 98 | 85 | 82 | 65 | 48 | 76 | 68 | 3 | 0 |
| 97.5 | 360 | 99 | 99 | 100 | 75 | 86 | 67 | 50 | 76 | 75 | 17 | 10 |
| 97.5 | 480 | 100 | 100 | 99 | 87 | 92 | 73 | 65 | 87 | 88 | 0 | 0 |
| 127.5 | 240 | 100 | 100 | 100 | 91 | 96 | 67 | 57 | 87 | 79 | 10 | 5 |
| 127.5 | 360 | 99 | 100 | 100 | 83 | 77 | 80 | 55 | 87 | 88 | 12 | 0 |
| 127.5 | 480 | 100 | 100 | 100 | 93 | 97 | 73 | 67 | 90 | 82 | 13 | 12 |
| ATR + MET – 1120 + 1120 | | 99 | 99 | 98 | 96 | 99 | 78 | 72 | 56 | 43 | 97 | 97 |
| ATR + MET – 2240 + 2240 | | 99 | 100 | 100 | 98 | 100 | 98 | 92 | 80 | 68 | 100 | 100 |

TABLE 6

| Dose Rates (g a.i/ha) | | 25DAT | 43DAT | 25DAT | 43DAT | 25DAT | 43DAT | 25DAT | 43DAT | 25DAT | 43DAT |
|---|---|---|---|---|---|---|---|---|---|---|---|
| Cpd A | Cpd B | SETFA | SETFA | SETLU | SETLU | SETVI | SETVI | SORVU | SORVU | XANST | XANST |
| 75 | 0 | 97 | 94 | 89 | 77 | 92 | 86 | 88 | 78 | 52 | 49 |
| 97.5 | 0 | 98 | 96 | 90 | 83 | 96 | 92 | 85 | 83 | 60 | 65 |
| 127.5 | 0 | 99 | 98 | 96 | 91 | 95 | 95 | 90 | 92 | 70 | 68 |
| 150 | 0 | 99 | 98 | 98 | 93 | 97 | 97 | 90 | 90 | 73 | 80 |
| 0 | 240 | 88 | 85 | 73 | 59 | 80 | 76 | 22 | 22 | 13 | 13 |

TABLE 6-continued

| Dose Rates (g a.i/ha) | | 25DAT | 43DAT | 25DAT | 43DAT | 25DAT | 43DAT | 25DAT | 43DAT | 25DAT | 43DAT |
|---|---|---|---|---|---|---|---|---|---|---|---|
| Cpd A | Cpd B | SETFA | SETFA | SETLU | SETLU | SETVI | SETVI | SORVU | SORVU | XANST | XANST |
| 0 | 360 | 93 | 84 | 79 | 56 | 92 | 84 | 43 | 30 | 13 | 16 |
| 0 | 480 | 95 | 59 | 88 | 75 | 92 | 90 | 60 | 55 | 16 | 11 |
| 0 | 600 | 96 | 94 | 89 | 85 | 95 | 94 | 72 | 40 | 17 | 8 |
| 75 | 240 | 97 | 94 | 95 | 89 | 95 | 92 | 77 | 75 | 50 | 25 |
| 75 | 360 | 99 | 98 | 97 | 97 | 97 | 96 | 88 | 83 | 50 | 38 |
| 75 | 480 | 98 | 98 | 97 | 95 | 97 | 97 | 82 | 78 | 49 | 38 |
| 97.5 | 240 | 98 | 97 | 93 | 92 | 96 | 94 | 82 | 78 | 61 | 50 |
| 97.5 | 360 | 98 | 97 | 96 | 94 | 96 | 95 | 82 | 73 | 55 | 49 |
| 97.5 | 480 | 100 | 99 | 98 | 97 | 99 | 99 | 87 | 83 | 64 | 58 |
| 127.5 | 240 | 99 | 98 | 98 | 95 | 97 | 96 | 83 | 70 | 63 | 58 |
| 127.5 | 360 | 100 | 100 | 99 | 99 | 99 | 98 | 87 | 82 | 72 | 73 |
| 127.5 | 480 | 99 | 99 | 98 | 98 | 98 | 97 | 87 | 72 | 74 | 73 |
| ATR + MET − 1120 + 1120 | | 97 | 96 | 95 | 88 | 96 | 96 | 60 | 50 | 31 | 32 |
| ATR + MET − 2240 + 2240 | | 99 | 99 | 98 | 96 | 98 | 98 | 73 | 52 | 65 | 76 |

These results demonstrate that the mixture of 4-benzoylisoxazole and Compound B, when compared with the commercial standard atrazine and metolachlor, remarkably provides a more effective level of weed control against a number of weed species at substantially reduced application rates of active ingredient, as well as possessing selectivity against the crop species maize.

What is claimed is:

1. A method of controlling the growth of weeds at a locus which comprises applying to said locus a synergistic herbicidally effective amount of:
   (a) a 4-benzoylisoxazole of formula (I):

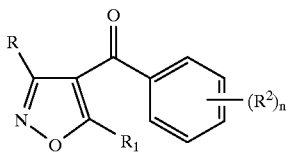

(I)

wherein
R is hydrogen or —$CO_2R^3$;
$R^1$ is cyclopropyl;
$R^2$ is selected from halogen, —$S(O)_p$Me and trifluoromethyl, n is two or three; p is zero, one or two; and
$R^3$ is $C_{1-4}$ alkyl; and
   (b) N-isopropyl-(5-trifluoromethyl-1,3,4-thiadiazol-2-yl)-4-(4'-fluoro-oxyacetanilide) having the formula (II):

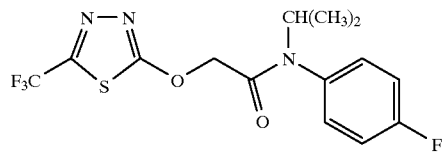

(II)

wherein the weight ratio of (a):(b) is from about 1:2000 to 50:1.

2. The method according to claim 1 wherein the 4-benzoylisoxazole derivative of formula I is 5-cyclopropyl-4-(2-methylsulphonyl-4-trifluoromethyl)benzoylisozaxole.

3. The method according to claim 1 using an application rate of from 5 to 500 g per hectare of 4-benzoylisoxazole and from 10 to 10,000 g per hectare of N-isopropyl-(5-trifluoromethyl-1,3,4-thiadiazol-2-yl)-4-(4'-fluoro-oxyacetanilide).

4. The method according to claim 1 wherein the locus is used, or to be used, for the growing of a crop.

5. The method according to claim 4 wherein the crop is maize.

6. The method according to claim 1 using an application rate of from about 5 to 200 g per hectare of 4-benzoylisoxazole and from about 50 to 5,000 g per hectare of N-isopropyl-(5-trifluoromethyl-1,3,4-thiadiazol-2-yl)-4-(4'-fluoro-oxyacetanilide).

7. The method according to claim 6 using an application rate of from about 50 to 130 g per hectare of 4-benzoylisoxazole and from about 80 to 875 g per hectare of N-isopropyl-(5-triuoromethyl-1,3,4-thiadiazol-2-yl)-4-(4'-fluoro-oxyacetanilide).

8. The method according to claim 7 using an application rate of from about 75 to 100 g per hectare of 4-benzoylisoxazole and from about 300 to 500 g per hectare of N-isopropyl-(5-trifluoromethyl-1,3,4-thiadiazol-2-yl)-4-(4'-fluoro-oxyacetanilide).

9. The method according to claim 1 by pre-emergence application.

10. A herbicidal composition comprising a synergistic herbicidally effective amount of:
    (a) a 4-benzoylisoxazole derivative of formula I as defined in claim 1; and
    (b) N-isopropyl-(5-trifluoromethyl-1,3,4-thiadiazol-2-yl)-4-(4'-fluoro-oxyacetanilide);
    wherein the weight ratio of (a):(b) is from about 1:2000 to 50:1;
    in association with a herbicidally acceptable diluent or carrier, a surface active agent; or a combination thereof.

11. The composition according to claim 10 wherein the 4-benzoylisoxazole derivative of formula I is 5-cyclopropyl-4-(2-methylsulphonyl-4-trifluoromethyl)benzoylisozaxole.

12. The composition according to claim 10 in which the weight ratio of (a):(b) is from about 1:1000 to 4:1.

13. The composition according to claim 12 in which the weight ratio of (a): (b) is from about 1:17.5 to 1.63:1.

14. The composition according to claim 13 in which the weight ratio of (a):(b) is from about 1:6.67 to 1:3.

15. The composition according to claim 10 in the form of a water dispersible granule.

16. A combination comprising a synergistic herbicidally effective amount of:

(a) a 4-benzoylisozaxole of formula I as defined in claim 1; and
(b) N-isopropyl-(5-trifluoromethyl-1,3,4-thiadiazol-2-yl)-4-(4'-fluoro-oxyacetanilide);

wherein the weight ratio of (a):(b) is from about 1:2000 to 50:1.

* * * * *